(12) United States Patent
Horvath et al.

(10) Patent No.: US 10,077,777 B2
(45) Date of Patent: Sep. 18, 2018

(54) ARTIFICIAL HEART SYSTEM IMPLEMENTING SUCTION RECOGNITION AND AVOIDANCE METHODS

(71) Applicant: THE CLEVELAND CLINIC FOUNDATION, Cleveland, OH (US)

(72) Inventors: David J. Horvath, Euclid, OH (US); Barry D. Kuban, Avon Lake, OH (US); Leonard A R Golding, Chagrin Falls, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 561 days.

(21) Appl. No.: 14/273,854

(22) Filed: May 9, 2014

(65) Prior Publication Data
US 2015/0322940 A1 Nov. 12, 2015

(51) Int. Cl.
| | | |
|---|---|---|
| *F04D 15/00* | (2006.01) | |
| *F04B 49/20* | (2006.01) | |
| *F04D 1/00* | (2006.01) | |
| *F04D 13/06* | (2006.01) | |
| *A61M 1/10* | (2006.01) | |

(52) U.S. Cl.
CPC ..... *F04D 15/0066* (2013.01); *F04D 15/0088* (2013.01); *A61M 1/101* (2013.01); *A61M 1/1029* (2014.02); *F04B 49/20* (2013.01); *F04D 1/006* (2013.01); *F04D 13/06* (2013.01)

(58) Field of Classification Search
CPC .... F04D 1/006; F04D 15/0066; F04D 29/042; F04D 7/02; F04D 13/06; F04D 13/064; F04D 13/0653; F04D 15/0088; F04D 27/001; F04D 27/004; F04B 49/06; F04B 49/065; F04B 49/10–49/106; F04B 49/20; G05D 16/2066; A61M 1/10; A61M 1/127; A61M 1/1086; A61M 1/101; A61M 1/1029–1/1031; A61M 1/12–1/122
USPC ...... 417/22, 42, 44.11; 623/3.13, 3.14, 3.28; 700/282
See application file for complete search history.

(56) References Cited

U.S. PATENT DOCUMENTS

| | | |
|---|---|---|
| 1,896,219 A | 2/1933 | Buckley |
| 1,959,106 A | 5/1934 | Messing |

(Continued)

FOREIGN PATENT DOCUMENTS

| | | |
|---|---|---|
| DE | 2733631 A1 | 2/1979 |
| GB | 1115210 | 5/1968 |

(Continued)

OTHER PUBLICATIONS

PCT International Search Report and Written Opinion for PCT/US2014/037465, dated Feb. 13, 2015, pp. 1-12.

(Continued)

*Primary Examiner* — Alexander Comley
(74) *Attorney, Agent, or Firm* — Tarolli, Sundheim, Covell & Tummino LLP

(57) ABSTRACT

A system and method of controlling the operation of a pump system includes modulating the speed of the pump and calculating a system condition parameter having a value related to the area of a hysteresis loop generated by a system operating parameter that varies in response to pump speed. The condition of the system is determined in response to the value of the system condition parameter.

19 Claims, 13 Drawing Sheets

(56) References Cited

U.S. PATENT DOCUMENTS

| | | |
|---|---|---|
| 3,410,218 A | 11/1968 | Fivel |
| 3,783,453 A | 1/1974 | Bolie |
| RE28,742 E | 3/1976 | Rafferty et al. |
| 4,355,954 A | 10/1982 | Wilson |
| 4,381,901 A | 5/1983 | Labudde |
| 4,392,777 A | 7/1983 | Huttlin |
| 4,589,822 A | 5/1986 | Clausen et al. |
| 4,752,183 A | 6/1988 | Sakurai |
| 4,867,633 A | 9/1989 | Gravelle |
| 4,888,011 A | 12/1989 | Kung et al. |
| 5,055,005 A | 10/1991 | Kletschka |
| 5,102,295 A | 4/1992 | Pope |
| 5,320,482 A | 6/1994 | Palmer et al. |
| 5,368,439 A | 11/1994 | Piazza |
| 5,507,629 A | 4/1996 | Jarvik |
| 5,695,471 A | 12/1997 | Wampler |
| 5,725,357 A | 3/1998 | Nakazeki et al. |
| 5,840,070 A | 11/1998 | Wampler |
| 5,863,179 A | 1/1999 | Westphal et al. |
| 5,888,242 A | 3/1999 | Antaki et al. |
| 5,928,131 A | 7/1999 | Prem |
| 6,074,180 A | 6/2000 | Khanwilkar et al. |
| 6,080,133 A | 6/2000 | Wampler |
| 6,142,752 A * | 11/2000 | Akamatsu ............ A61M 1/101 417/44.2 |
| 6,171,078 B1 | 1/2001 | Schob |
| 6,179,733 B1 | 1/2001 | Story |
| 6,193,473 B1 | 2/2001 | Mruk et al. |
| 6,220,832 B1 | 4/2001 | Schob |
| 6,234,998 B1 | 5/2001 | Wampler |
| 6,244,835 B1 | 6/2001 | Antaki et al. |
| 6,293,901 B1 | 9/2001 | Prem |
| 6,363,276 B1 | 3/2002 | Prem et al. |
| 6,368,083 B1 | 4/2002 | Wampler |
| 6,375,607 B1 | 4/2002 | Prem |
| 6,394,769 B1 | 5/2002 | Bearnson et al. |
| 6,422,838 B1 | 7/2002 | Sloteman |
| 6,422,990 B1 | 7/2002 | Prem |
| 6,511,298 B2 | 1/2003 | Takura et al. |
| 6,551,058 B2 | 4/2003 | Nowack |
| 6,595,762 B2 | 7/2003 | Khanwilkar et al. |
| 6,619,935 B1 | 9/2003 | Kluth et al. |
| 6,638,031 B1 | 10/2003 | Humburg |
| 6,672,846 B2 | 1/2004 | Rajendran et al. |
| 6,688,861 B2 | 2/2004 | Wampler |
| 6,746,416 B2 | 6/2004 | Hubbard et al. |
| 7,175,588 B2 | 2/2007 | Morello |
| 7,189,260 B2 | 3/2007 | Horvath et al. |
| 7,435,059 B2 | 10/2008 | Smith et al. |
| 7,502,648 B2 | 3/2009 | Okubo et al. |
| 7,704,054 B2 | 4/2010 | Horvath et al. |
| 8,210,829 B2 | 7/2012 | Horvath et al. |
| 8,657,874 B2 | 2/2014 | Horvath et al. |
| 2002/0102169 A1 | 8/2002 | Wampler |
| 2004/0047736 A1* | 3/2004 | Nose .................. F04B 49/06 417/44.1 |
| 2004/0133061 A1* | 7/2004 | Nose .................. A61M 1/122 600/16 |
| 2004/0234397 A1 | 11/2004 | Wampler |
| 2006/0183962 A1 | 8/2006 | Okubo et al. |
| 2007/0253842 A1* | 11/2007 | Horvath ............... F04D 1/06 417/350 |
| 2010/0168848 A1* | 7/2010 | Horvath .............. F04D 29/042 623/3.13 |
| 2010/0174231 A1* | 7/2010 | Horvath .............. A61M 1/1086 604/67 |
| 2010/0180951 A1* | 7/2010 | Smirnov .............. G05D 7/0635 137/2 |
| 2012/0245681 A1* | 9/2012 | Casas .................. A61M 1/101 623/3.28 |

FOREIGN PATENT DOCUMENTS

| | | |
|---|---|---|
| JP | 54020214 A | 2/1979 |
| JP | 59133735 A | 8/1984 |
| JP | 63189692 A | 8/1988 |
| WO | 2004098677 A1 | 11/2004 |
| WO | 2006053384 A1 | 5/2006 |

OTHER PUBLICATIONS

Endo et al., "A Safe Automatic Driving Method for a Continuous Flow Ventricular Assist Device Based on Motor Current Pulsatility: In Vitro Evaluation", American Society of Artificial Internal Organs Journal, 2002, pp. 83-89.

Ferreira et al., "A Control System for Rotary Blood Pumps Based on Suction Detection", IEEE Transactions on Biomedical Engineering, 2009, vol. 56, No. 3, pp. 656-665.

Ferreira et al., "A Discriminant-Analysis-Based Suction Detection System for Rotary Blood Pumps", Proceedings of the 28th IEEE EMBS Annual International Conference, 2006, pp. 5382-5385.

Gao et al., "An Anti-Suction Control for an Infra-Aorta Pump Using Blood Assistant Index: A Numerical Simulation", Artificial Organs, 2012, vol. 36, No. 3, pp. 275-290.

Frazier et al., "Total Heart Replacement with Dual Centrifugal Ventricular Assist Devices", American Society of Artificial Internal Organs Journal, 2005, pp. 224-229.

Karantonis et al., "Identification and Classification of Physiologically Significant Pumping States in an Implantable Rotary Blood Pump", Artificial Organs, 2006, vol. 30, No. 9, pp. 671-679.

Khalil et al., "Continous Flow Total Artificial Heart: Modeling and Feedback Control in a Mock Circulatory System", American Society of Artificial Internal Organs Journal, 2008, pp. 249-255.

Larose et al., "Design Concepts and Principle of Operation of the HeartWare Ventricular Assist System", American Society of Artificial Internal Organs Journal, 2010, pp. 285-289.

Naiyanetr et al., "Focus Issue: Mechanical Circulatory Support Continuous Assessment of Cardiac Function During Rotary Blood Pump Support: A Contractility Index Derived from Pump Flow", Journal of Heart and Lung Transplantation, 2010, vol. 29, Issue 1, pp. 37-44.

Ng et al., "Evaluation of Suction Detection During Different Pumping States in an Implantable Rotary Blood Pump", Artificial Organs, 2013, pp. 1-10.

Qian et al., "A Novel Permanent Maglev Impeller TAH: Most Requirements on Blood Pumps Have Been Satisfied", Journal of Biomaterials Applications, 2003, vol. 18, pp. 53-61.

Schima PhD et al., "First Clinical Experience with an Automatic Control System for Rotary Blood Pumps During Ergometry and Right-Heart Catheterization", The Journal of Heart and Lung Transplantation, 2006, pp. 167-173.

Voigt et al., "Suction Detection for the MicroMed DeBakey Left Ventricular Assist Device", American Society of Artificial Internal Organs Journal, 2005, pp. 321-328.

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

Vollkron PhD et al., "Suction Events During Left Ventricular Support and Ventricular Arrhythmias", The Journal of Heart and Lung Transplantation, 2007, pp. 819-825.

Wang et al., "Detection of Ventricular Suction in an Implantable Rotary Blood Pump Using Support Vector Machines", 33rd Annual International Conference of the IEEE EMBS, 2001, pp. 3318-3321.

Yuhki et al., "Detection of Suction and Regurgitation of the Implantable Centrifugal Pump Based on the Motor Current Waveform Analysis and Its Application to Optimization of Pump Flow", Artificial Organs, 1999, vol. 23, No. 6, pp. 532-537.

* cited by examiner

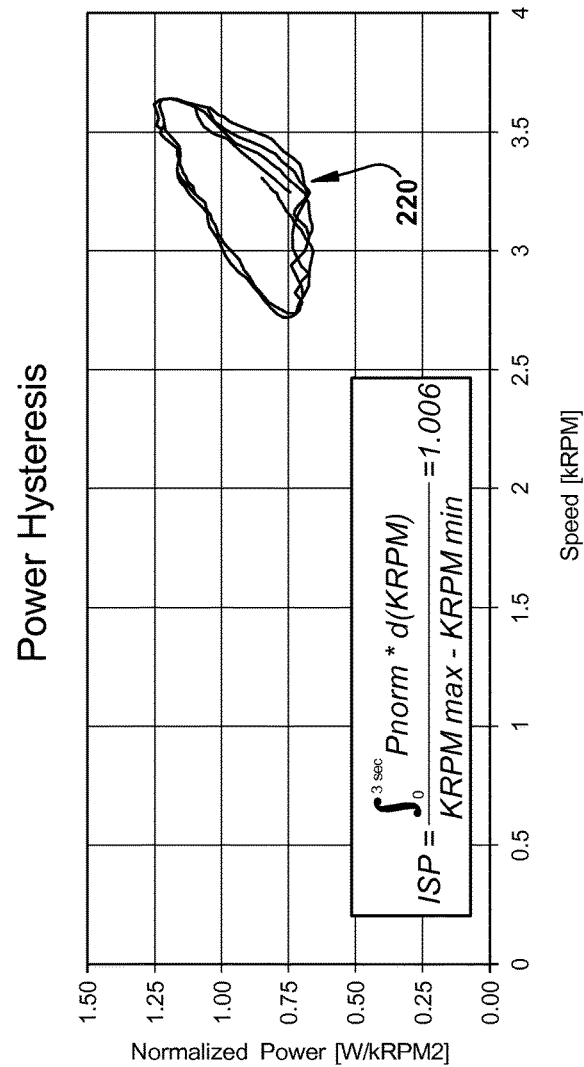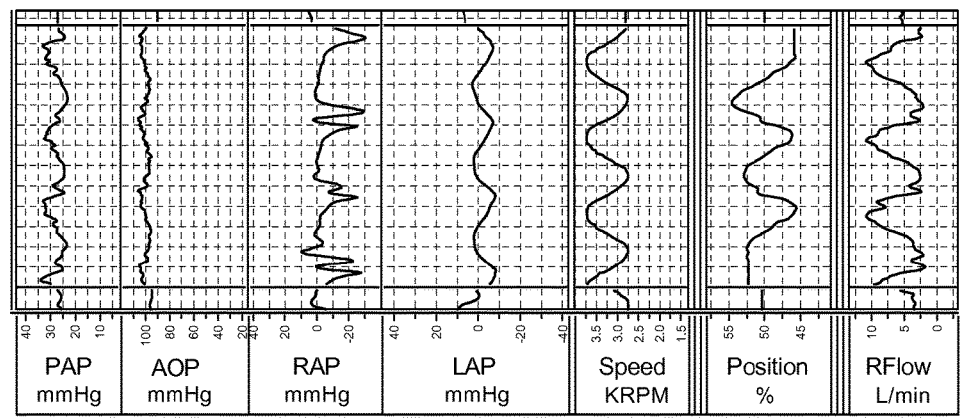
Fig. 8B
Fig. 8A

ARTIFICIAL HEART SYSTEM IMPLEMENTING SUCTION RECOGNITION AND AVOIDANCE METHODS

GOVERNMENT FUNDING

This invention was made with government support under HL096619 and HL089052 awarded by the National Institutes of Health. The government has certain rights in the invention.

FIELD OF THE INVENTION

This invention relates generally to artificial heart systems. More particularly, the invention relates to systems and methods for controlling blood pumps implemented in artificial heart systems.

BACKGROUND OF THE INVENTION

Heart transplant is a course of action for patients with end stage heart failure, a leading cause of premature death. Due to the unavailability of donor hearts, electromechanical blood pumping systems are being developed and are increasingly coming into use. These devices can provide a bridge to transplant, a bridge to recovery, or a permanent treatment for patients who may not receive a donor heart. Most of these patients will be treated with a ventricular assist device ("VAD"), which assists the beating heart by drawing blood from the left or right ventricle and discharging the blood to the aorta or pulmonary artery, respectively. Some patients require a total artificial heart (TAH), which replaces the patient's heart, as a bridge to transplant or as a permanent therapy.

One known type of TAH is a continuous flow total artificial heart (CFTAH). The CFTAH includes two centrifugal pumps on one rotor supported on a hydrodynamic bearing and driven by a single motor. The CFTAH replaces the ventricles of the heart, and delivers blood flow to both the systemic (left) and pulmonary (right) circulation of the patient. Examples of CFTAH pumps are described in U.S. Pat. No. 8,210,829 B2 and U.S. Pat. No. 7,704,054 B2, and in U.S. Patent Application Publications US 2010/0174231 A1 and US 2012/0328460 A1.

CFTAH implementation can be performed by surgically excising the ventricles and connecting the left and right pump inlets to the left and right atria, respectively, and connecting the left and right pump outlets to the aorta and pulmonary artery, respectively. During the operation of the CFTAH, care must be exercised to avoid a suction condition in which atrial tissue is sucked into the pump inlet, thereby blocking flow into the pumping chamber and causing an imbalance in systemic and pulmonary blood flow. In addition to the obvious physiological problems brought on by this condition, suction conditions can lead to the pump rotor shifting axially onto a thrust bearing which can lead to hemolysis and/or thrombosis.

While this type of CFTAH can be operated under external control, it is desirable for the system to respond automatically to physiologic changes, preferably using the least number of sensors. Additionally, in the physiologic control scheme, there is a need to detect conditions, such as tissue suction at the pump inlets, that may jeopardize the patient.

BRIEF SUMMARY OF THE INVENTION

Three different mathematical algorithms are described to recognize suction by evaluating the pump response to modulating speed.

According to one aspect of the invention, a position sensor monitors the axial position of the rotating assembly magnet, and a suction condition is recognized by characteristics in the hysteresis loop of position sensor output versus speed.

According to a second aspect of the invention, a suction condition is recognized by characteristics in the hysteresis loop of pump power versus speed.

According to a third aspect of the invention, a suction condition is recognized by statistically comparing the motor current wave form to the speed input wave form.

According to one aspect, a method of controlling the operation of a pump system includes modulating the speed of the pump, and calculating a system condition parameter having a value related to a hysteresis loop generated by a system operating parameter that varies in response to pump speed. The condition of the system is determined in response to the value of the system condition parameter.

According to another aspect, the system operating parameter is the pump rotor axial position. According to this aspect, the system condition parameter is calculated according to:

$$ISP = \frac{\int_{t=0}^{t=n\,sec} L(t)dN}{N_{max} - N_{min}}$$

wherein L(t) is the pump rotor axial position, $N_{max}-N_{min}$ is the modulated speed range, and n sec is the time interval of the integral in seconds (e.g., 3 seconds).

According to another aspect, the system operating parameter is motor power of the pump. According to this aspect, the system condition parameter is calculated according to:

$$ISP = \frac{\int_{t=0}^{t=n\,sec} \frac{P(t)}{N(t)^2} dN}{N_{max} - N_{min}}$$

wherein P(t) is the pump motor power, N(t) is the pump speed, $N_{max}-N_{min}$ is the modulated speed range, and n sec is the time interval of the integral in seconds (e.g., 3 seconds).

According to another aspect, the step of determining the condition of the system includes the step of determining a pump inlet suction condition. According to this aspect, the step of correcting the condition of the system includes the step of reducing the speed of the pump in response to determining a pump inlet suction condition.

According to another aspect, the step of determining the condition of the system includes the step of determining a deviation in the system condition parameter.

According to another aspect, the step of determining the condition of the system includes the steps of repeating the calculation of the system condition parameter over several iterations, and determining when the value of a current iteration of the calculated system condition parameter deviates from a limit value by a predetermined amount.

According to another aspect, the step of modulating the speed of the pump includes the step of modulating the speed with an integer number of modulations within a time window having a predetermined length.

According to another aspect, the pump is a blood pump.

According to another aspect, the invention is a pump system including a pump and a controller for controlling the operation of the pump. The controller is adapted to calculate a system condition parameter having a value related to a hysteresis loop generated by a system operating parameter that varies in response to pump speed. The controller is further adapted to determine the condition of the system in response to the value of the system condition parameter.

According to another aspect, the system operating parameter includes the pump rotor axial position. According to this aspect, the system condition parameter is calculated according to:

$$ISP = \frac{\int_{t=0}^{t=n\,sec} L(t)dN}{N_{max} - N_{min}}$$

wherein L(t) is the pump rotor axial position, $N_{max}$-$N_{min}$ is the modulated speed range, and n sec is the time interval of the integral in seconds (e.g., 3 seconds).

According to another aspect, the system operating parameter includes motor power of the pump. According to this aspect, the system condition parameter is calculated according to:

$$ISP = \frac{\int_{t=0}^{t=n\,sec} \frac{P(t)}{N(t)^2}dN}{N_{max} - N_{min}}$$

wherein P(t) is the pump motor power, N(t) is the pump speed, $N_{max}$-$N_{min}$ is the modulated speed range, and n sec is the time interval of the integral in seconds (e.g., 3 seconds).

According to another aspect, the controller is adapted to determine the condition of the system in response to determining a pump inlet suction condition.

According to another aspect, the controller is adapted to determine the condition of the system in response to determining a deviation in the system condition parameter.

According to another aspect, to determine the condition of the system, the controller is adapted to repeat the calculation of the system condition parameter over several iterations, and determine when the value of a current iteration of the calculated system condition parameter deviates from a limit value by a predetermined amount.

According to another aspect, the controller is adapted to modulate the speed of the pump by modulating the speed with an integer number of modulations within a time window having a predetermined length.

According to another aspect, the pump of the system is a blood pump.

According to another aspect, the pump includes an electrical motor coupled to a rotor that carries first and second impellers at opposite ends thereof.

According to another aspect, the pump is an artificial heart, wherein the first impeller communicates with a patient's systemic vasculature and the second impeller communicates with the patient's pulmonary vasculature. The pump is operable to circulate blood from the first impeller through the systemic vasculature to the second impeller, and from the second impeller through the pulmonary vasculature back to the first impeller.

BRIEF DESCRIPTION OF THE DRAWINGS

The invention may be best understood by reference to the following description taken in conjunction with the accompanying drawing figures in which:

FIGS. 7A-9B are charts that illustrate various physiological conditions and pump operating parameters of the pump, and the identification of any associated pump inlet suction, according to another aspect of the invention.

DETAILED DESCRIPTION OF THE INVENTION

Figure 1:
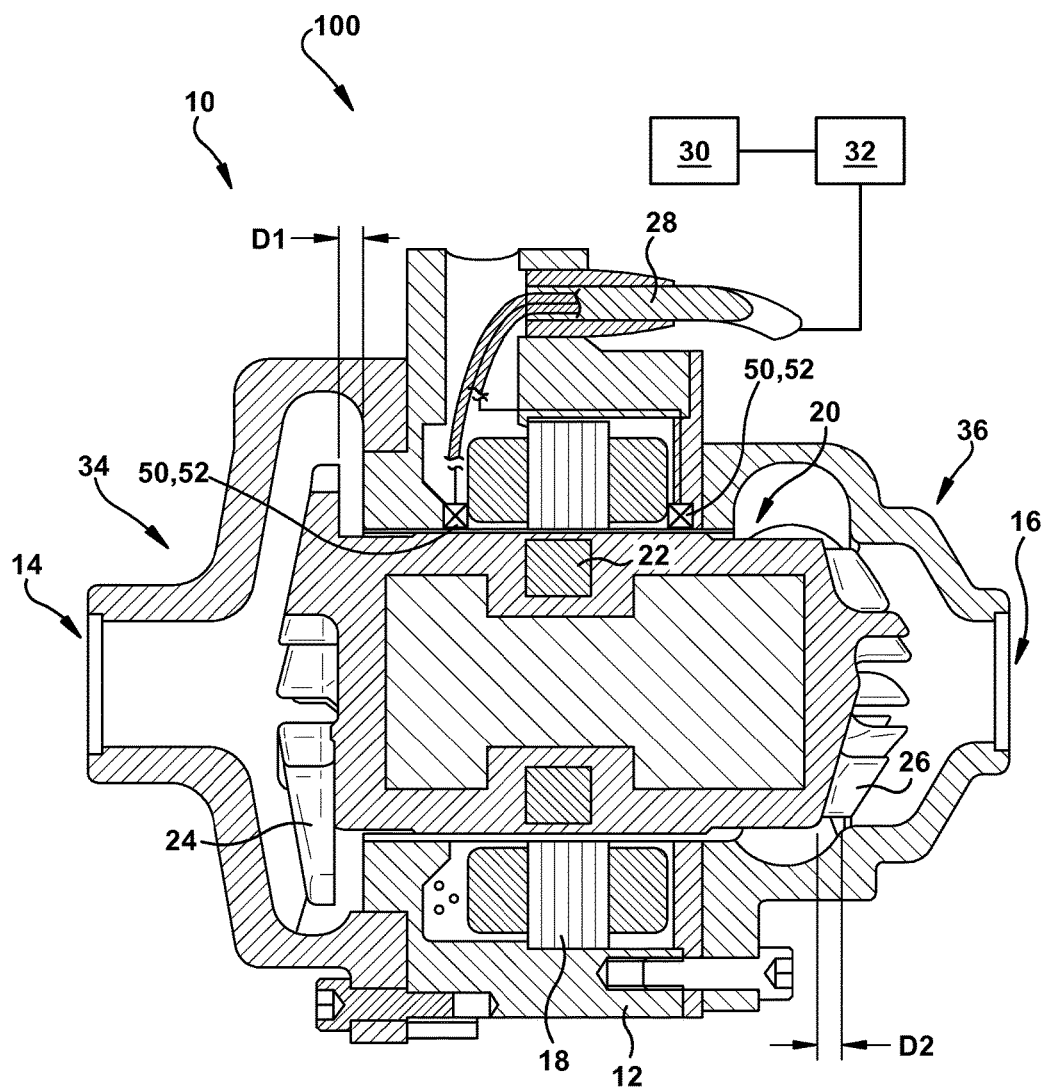
FIG. 1 is a schematic illustration of a total artificial heart system including a cross-sectional view of a blood pump portion of the system, according to an aspect of the invention.

Referring to the drawings in which identical reference numerals denote the same elements throughout the various views, FIG. 1 depicts an example of a total artificial heart system 100. The artificial heart system 100 includes a continuous flow total artificial heart in the form of a two-stage centrifugal blood pump 10 that is used to temporarily or permanently support a human patient. The blood pump 10 replaces the native left and right ventricles and valves, which are surgically excised or removed, and is adapted to connect the left and right pump inlets to the remaining atria.

The blood pump 10 includes a hollow housing 12 with opposed left and right inlets 14 and 16. An electrical stator 18 comprising a plurality of coil windings is disposed in the housing 12. While a total blood pump 10 is used as an illustrative example, the principles of the invention are equally applicable to other kinds of mechanical configurations and pumps, for example ventricular assist devices.

A rotating assembly 20 or "rotor" is disposed inside the stator 18. The rotor 20 includes a magnet assembly 22 comprising one or more permanent magnets arranged in an annular configuration. A left impeller 24 comprising an annular array of vanes is carried at the left end of the rotor 20 adjacent the left inlet 14. A right impeller 26 comprising an annular array of vanes is carried at the right end of the rotor 20 adjacent the right inlet 16. The left and right impellers 24 and 26 discharge into separate right and left peripheral outlets, which are not shown in FIG. 1.

The left impeller 24 along with the portion of the housing 12 surrounding it can be referred to as a left pump 34 while the right impeller 26 along with the portion of the housing 12 surrounding it can be referred to as a right pump 36. Being components of the same rotating assembly, the left pump 34 and right pump 36 operate at the same speed. The left pump 34 includes the left inlet 14 and the right pump 36 includes the right inlet 16.

All of the portions of the blood pump 10 that can come into contact with blood or tissue can be constructed from known biologically compatible materials such as titanium, medical grade polymers, synthetic jewel materials, and the like.

The rotor 20 and the stator 18 operate as a brushless DC motor through the application of varying electrical currents to the stator 18. The blood pump 10 is coupled by a cable 28 to a controller 32, which is in turn powered by a power source 30, for example a battery, both of which are shown schematically in FIG. 1. The controller 32 is operative to control the operation of the blood pump and also to perform the system monitoring and condition detection functions described herein. More specifically, the controller 32 can also perform the suction recognition and avoidance methods described herein.

The controller 32 can have any configuration suited to perform the pump operation and control methodologies described herein. For example, the controller can include a computer, such as a personal computer (PC), that communicates with a commercially available motor driver that is connected to the blood pump 10. In this configuration, the PC would provide instructions (e.g., a motor speed demand signal or set point) to the motor driver, which would drive the motor in response to the instructions. For instance, in one implementation, the PC can provide a demand signal/set point to the motor driver, and the motor driver can modulate a motor driver signal to drive the motor to the requested speed. In this manner, an oscillating motor speed can be achieved via an oscillating motor driver signal. In this implementation, the computer component of the controller 32 thus performs high level controls (e.g., demand signal calculation), and the motor driver performs low level controls (e.g., modulate the motor driver signal to achieve the requested speed). Those skilled in the art will appreciate that the controller 32 could have an alternative configuration, such as one in which the controller is a custom, application specific standalone unit that includes both the computer and motor driver portions that function as described above.

Regardless of its configuration, for the brushless DC motor configuration of the pump 10, the controller 32 is effective to provide pulsed DC current to the stator 18 in a known manner. The degrees of freedom with which the controller 32 can operate the pump can be the mean pump speed (RPM), speed pulse rate, speed pulsatility (i.e., RPM modulation about the mean), and/or duty cycle. Additionally, with feedback received either directly from the pump or indirectly via the motor driver, the computer can perform the system monitoring and condition detection functions, such as the suction recognition and avoidance functions that are described herein. The controller 32 can be further configured to measure one or more system operating parameters, such as electrical power (wattage) delivered to the blood pump 10, pump rotor axial position and pump speed. Speed pulsatility (i.e., RPM modulation) may be used to create a pulse in a patient, and also provide an additional parameter for physiologic control.

Figure 2:
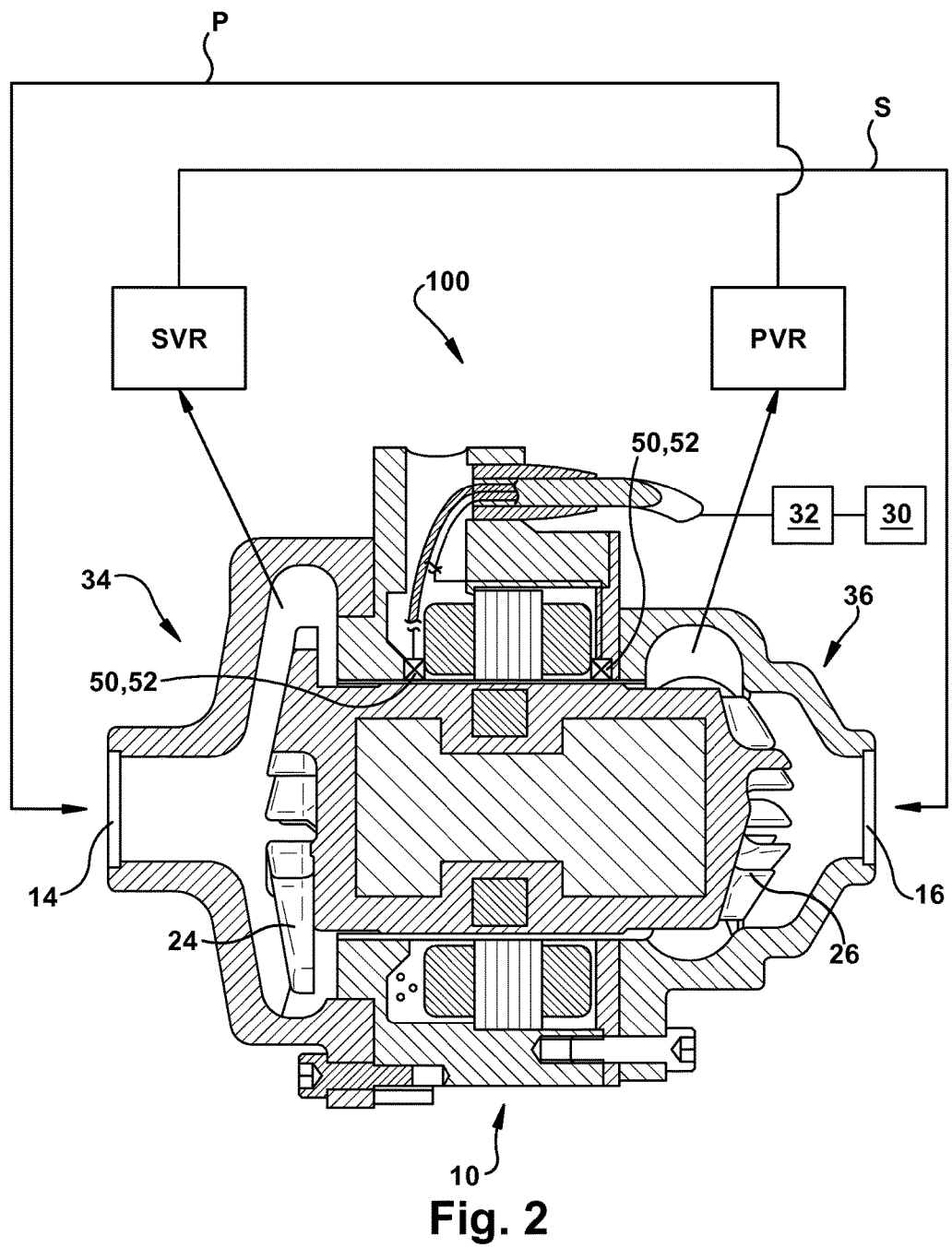
FIG. 2 is schematic illustration of the total artificial heart system of FIG. 1, illustrating the implementation of the system in a patient, according to another aspect of the invention.

FIG. 2 shows a simplified schematic of the blood pump 10 coupled to a patient's circulatory system. In operation, the left pump 34 pushes blood through the body's systemic vasculature, which defines a fluid circuit "S" and is represented from a hydraulic standpoint by a systemic vascular resistance labeled "SVR". Blood then flows back to the right inlet 16 via the right atrium. The right pump 36 pushes the blood through the body's pulmonary vasculature, which defines another fluid circuit "P" and is represented from a hydraulic standpoint by a pulmonary vascular resistance labeled "PVR". Blood flows from the PVR back to the left inlet 14 via left atrium.

If the systemic (i.e., left) flow is lower than the pulmonary (i.e., right) flow, then the left atrial pressure increases, and the right atrial pressure decreases. If the left output is greater than the right, then the atrial pressures reverse. Thus, an unbalance in flows is automatically accompanied by an unbalance in atrial (pump inlet) pressures.

The magnet assembly 22 in the rotor 20 is axially shorter than the stator 18, allowing a degree of free axial movement of the rotor 20, in response to any unbalance of pump inlet (i.e., atrial) pressures. This axial movement changes the distances "D1" and "D2" (see FIG. 1) which represent axial operating clearances of the left impeller 24 and aperture opening at the OD of the right impeller 26, respectively. This change in pump geometry affects the relative left/right performance in a direction to correct the atrial pressure imbalance. Thus, the blood pump 10 is self-balancing, acting as an inlet pressure balancing regulator while at the same time pumping both systemic and pulmonary circulation. The blood pump 10 may thus be constructed and operate in accordance with the construction and principles of operation detailed in the aforementioned U.S. Pat. No. 8,210,829 B2 and U.S. Pat. No. 7,704,054 B2, and U.S. Patent Application Publications US 2010/0174231 A1 and US 2012/0328460 A1, the disclosures of which are hereby incorporated by reference in their entireties.

The blood pump 10 is controlled in a known manner to deliver a volumetric flow rate of blood to the systemic vasculature. An example of a system and method for controlling the operation of the blood pump 10 is described in US 2010/0174231 A1, the disclosure of which is hereby incorporated by reference in its entirety. Under the control method, the controller 32 delivers power to the blood pump 10 to rotate the left and right impellers 24 and 26, and the speed of the rotor may be modulated in order to create pulsatory flow in the patient. Independent of the control process, the self-balancing characteristics take place throughout operation of the blood pump 10.

With the use of continuous flow blood pumps, there is a patient hazard associated with suction of tissue around the pump inlets, creating a sudden blockage to pump flow. Avoiding these suction conditions is fundamental to the successful use of continuous flow blood pumps. Some current approaches to pump control involve the sensing of insipient suction by signal analysis of pump flow, pump power, or pump current and immediately decrementing pump speed to avoid the suction event. Problems with this approach stem from the fact that the physical condition of the patient can change over time, resulting in varying vascular resistances that inherently produce fluctuations in the flow, power, and current variables of the pump. These fluctuations can lead to false identification of suction events, which can prompt unnecessary responses. None of these approaches use speed modulation as a forcing function for the diagnostic method.

According to the invention, the artificial heart system 100 is constructed and configured to identify and respond to inlet suction conditions by monitoring hysteresis in certain operating parameters of the system. Hysteresis relates to the idea that the operation, function, or condition of a system lags behind the forcing function input driving the system. If a given input in the system alternately increases and decreases, operating parameters of the system that depend on or respond to the input tend to form a loop when viewed graphically over time. These loops, for example, can occur because of a dynamic lag between the input and the response of the operating parameter. The lag depends on the frequency of change of the input, and goes toward zero as the frequency decreases. Based on these principles, a system condition parameter having a value related to the hysteresis loop for a system operating parameter that varies in response to an input to the pump system can be used to identify a condition of the pump system.

Testing Method

To test the hysteresis suction identification and avoidance algorithms of the artificial heart system 100, the blood pump 10 was implanted in an in-vivo subject (calf). The in-vivo subject was subjected to physiologic excursions to evaluate the performance of the hysteresis suction identification and avoidance algorithms.

Rotor Position Hysteresis Suction Identification

One system operating parameter for which hysteresis can be used to calculate a system condition parameter is rotor axial position. According to this aspect of the invention, the controller 32 can implement an algorithm that identifies a suction condition based on rotor position hysteresis. To achieve this, referring to FIG. 1, the blood pump 10 can be outfitted with a rotor position sensor 50. The position sensor 50 comprises one or more Hall effect sensors 52 that detect the presence and magnitude of magnetic fields acting on the sensors. The Hall effect sensors 52 are mounted in the housing 12 on opposite sides of the rotor magnet 22 and wired to the controller 32 via the cable 28. As the rotor 20 moves axially in the housing 12, the magnet 22 moves closer to one of the sensors 52 and away from the other of the sensors. The differential between the magnitudes of the magnetic fields measured by the Hall effect sensors 52 is indicative of the axial position of the rotor 20. The controller 32 measures and calculates this differential and determines the corresponding axial position of the rotor 20 in real time during operation of the blood pump 10.

According to this aspect of the invention, the position sensor 50 provides a real time signal indicative of the axial position of the rotor 20. Suction at one or more of the pump inlets 14, 16 can be identified by implementing a modulating pump speed and monitoring a hysteresis loop of the resulting axial position of the rotor 20. Modulating the pump speed modulates the systemic and pulmonary pressures, which causes the rotor to oscillate axially. Viewing rotor position with respect to pump speed over time, this oscillation presents as a hysteresis loop that can be monitored by the controller 32 via data acquired by the rotor position sensor 50.

Under normal pump operating conditions, the hysteresis loop will take on a general shape that does not deviate significantly unless the conditions of the physiology of the patient or the conditions of the artificial heart system 100 change. Even so, slight or gradual changes in these conditions are expected, so the shape of the hysteresis loop would be expected to change correspondingly slightly or gradually over time. Deviations in the shape of the hysteresis loop that fall outside these expected changes to a significant degree can be indicative of a suction event. According to this aspect of the invention, the artificial heart system 100 is constructed and configured to monitor the shape of the hysteresis loop for deviations from the expected shape.

Recognizing that the shape of the loop affects the area of the loop, to accomplish this, an integral equation is implemented by the controller 32. This integral equation calculates the area within the loop at a predetermined frequency. This area is summed within a moving time window, such as a 3-second moving window. Shorter or longer windows could be implemented. Deviations in the calculated hysteresis loop from the values expected based on the moving window can be characterized as indicating a suction condition.

For example, according to one implementation, the controller 32 can acquire data points at a predetermined frequency, such as 100 Hz or 200 Hz, to form or otherwise identify the hysteresis loop. The controller 32 can calculate the area within the loop over a 3-second window. Within this window, the controller 32 can calculate the area at a predetermined frequency, such as once per second or once per speed modulation. Thus, for example, with a 3-second window, the controller 32 could perform an integral calculation, every second, of the area within the loop for the last three seconds. As the window moves along in time, new loop calculations are added and the oldest is removed on a first-in, first-out basis, thus creating a moving 3-second window. Each new loop area calculation can be compared to one or more of the previously calculated loop areas or to a composite or average of the previous loop areas. If the area of the new loop deviates by a predetermined amount from a limit value (determined empirically or by a physician), this can indicate a suction event and the controller 32 can respond appropriately, e.g., by producing an alarm and reducing pump speed.

According to this aspect of the invention, the rotor position vs. speed characteristics of the system 100 are monitored via a hysteresis loop. To accomplish this, the controller 32 can implement a computer program to calculate a system condition parameter in the form of an Impending Suction Parameter (ISP) to evaluate hysteresis in the system operating parameter. In this case, the system operating parameter is the rotor axial position. According to this aspect, the ISP is tested against a limit value to identify the occurrence or impending occurrence of a suction event and trigger a speed control response. An example of the calculation used to determine the ISP is illustrated below:

$$ISP = \frac{\int_{t=0}^{t=n\,sec} L(t)dN}{N_{max} - N_{min}} \text{ (mm)} \quad \text{(Equation 1)}$$

where L(t) is the relative axial location of the rotating assembly indicated by the position sensor 50, $N_{max}-N_{min}$ is the modulated speed range, and n sec is the time interval of the integral in seconds (e.g., 3 seconds).

The integration can be performed within the controller 32 in any known manner. For example, the controller 32 can perform a simple numerical integration method, such as the Trapezoidal Rule or Simpson's Rule. The speed modulation rate can, for example, be set to a convenient rate, such as 60, 80, 100, or 120 BPM, so that there will be an integer number (n=3, 4, 5 or 6) of speed modulation cycles over the 3-second integration period. Other known integration methods, such as Boole's Rule, Hardy's Rule, Newton-Cotes Formulas, Simpson's ⅜ Rule, or Weddle's Rule could also be utilized. The integration period could also be increased or decreased, and alternative speed modulation rates could be selected.

Figure 3:
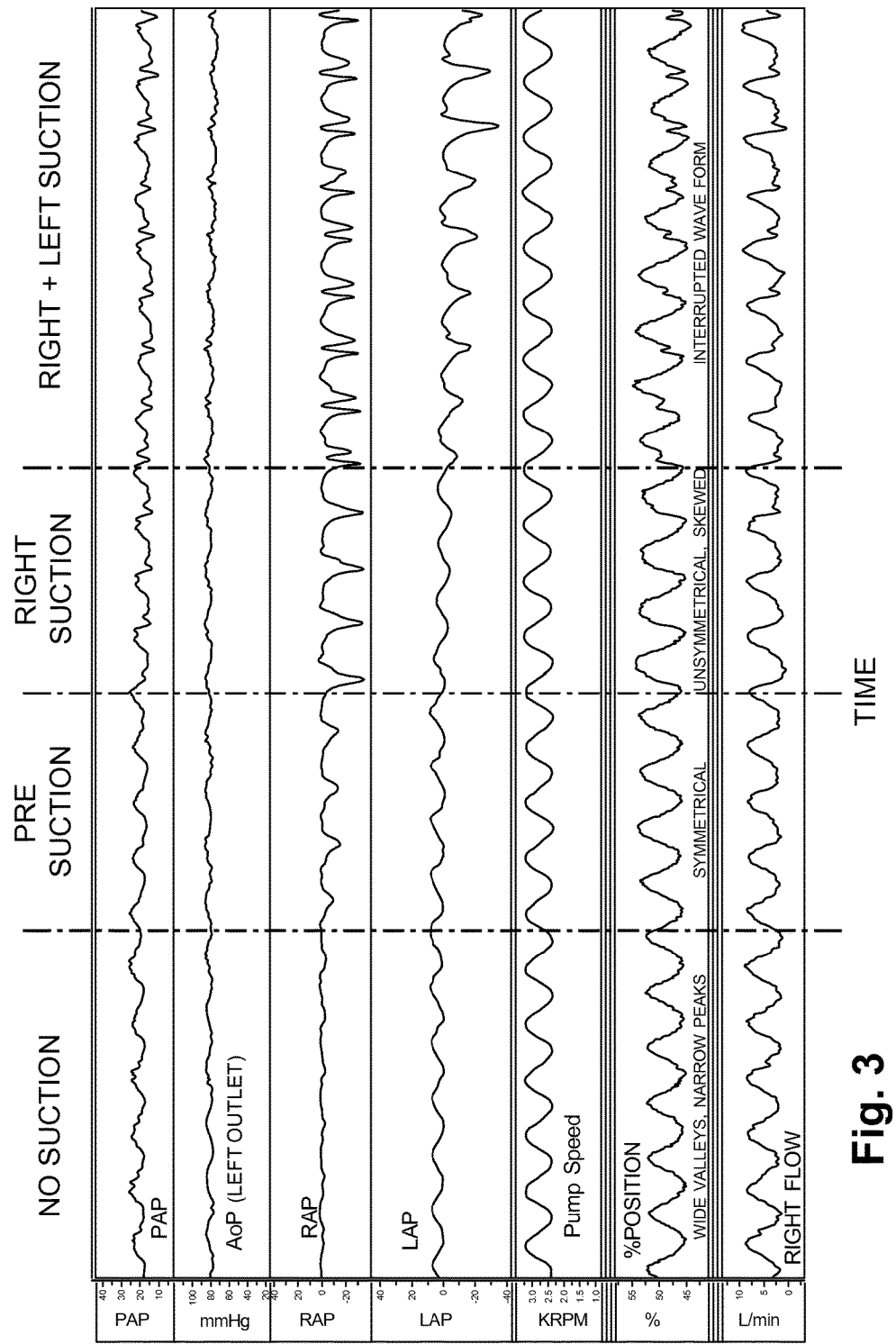
FIG. 3 is a chart illustrating various physiological conditions and pump operating parameters at varying stages of inlet suction conditions of the pump.

FIG. 3 illustrates certain in-vivo physiological and pump characteristics during operation of the blood pump 10 in the in-vivo subject. The physiological and pump characteristics illustrated in FIG. 3 include pulmonary arterial pressure or "PAP" (mmHg), aortic (left outlet) pressure or "AoP" (mmHg), right atrial pressure or "RAP" (mmHg), left atrial pressure or "LAP" (mmHg), motor speed (krpm), rotor position, and right flow (liter/min, LPM). The chart is divided over time, from left to right, to illustrate varying conditions of inlet suction. These conditions range from no suction, to pre-suction (i.e., obstruction approaching), to suction at the right inlet 16, to suction at both the right inlet and left inlet 14.

Viewing the no suction condition, it is readily apparent that as the pump speed is modulated, there is a corresponding modulation in the physiological and pump characteristics and system operating parameters, including the relative axial position of the rotor detected by the position sensor 50. The modulation in these characteristics/parameters varies in amplitude, but their periods are approximately equal to that of the modulated speed. Of particular note is that the phase of these characteristics/parameters is shifted from the modulated speed. This illustrates the dependent, time-shifted nature of these interrelated characteristics/parameters which gives rise to hysteresis in the system. In the normal operation of the system 100, the position signal is characterized as being symmetrical, with wide valleys and narrow peaks.

Figure 4:
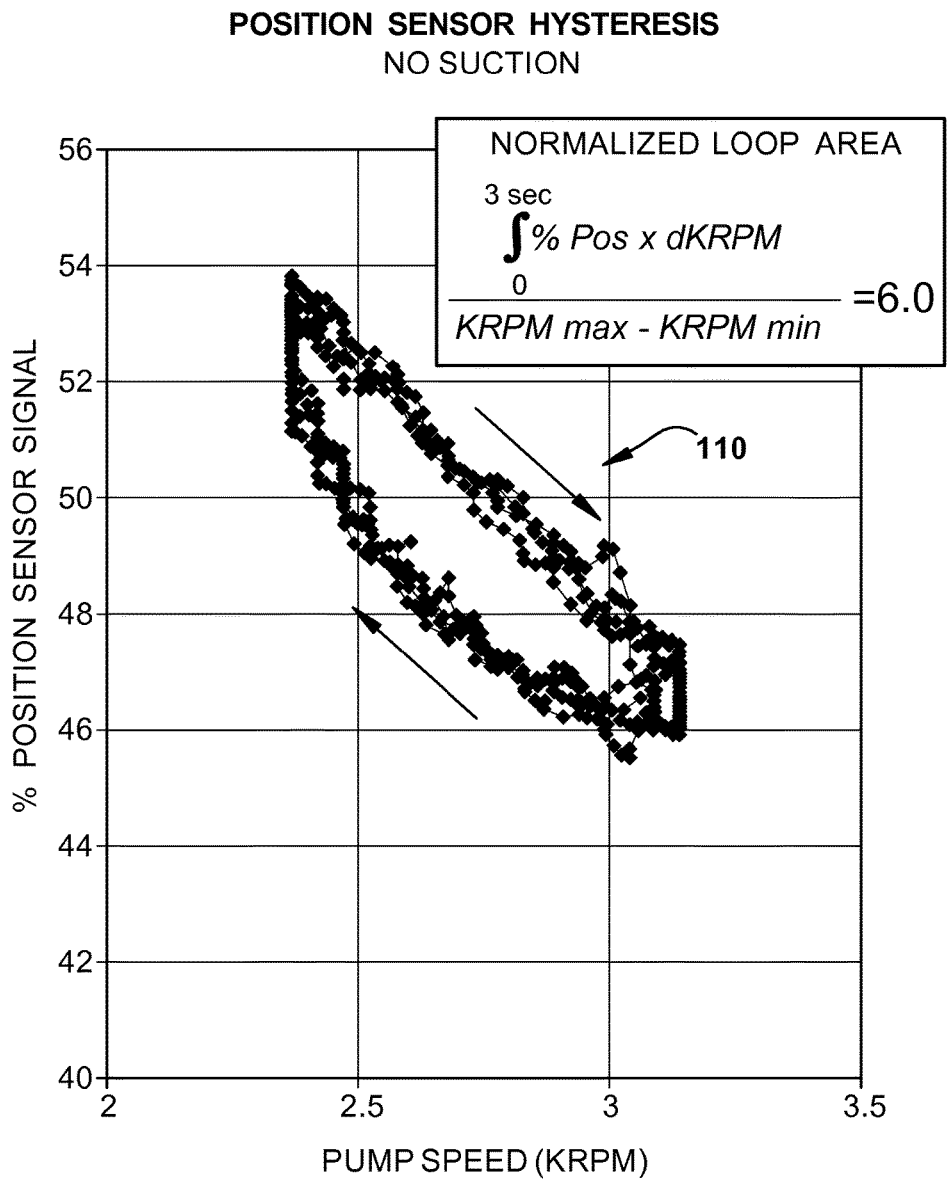
FIGS. 4-6 are charts that illustrate the identification of the varying stages of pump inlet suction illustrated in FIG. 3, according to another aspect of the invention.

FIG. 4 is a plot that illustrates the pump rotor position versus speed during operation of the blood pump 10 in a no suction condition, such as the no suction condition illustrated in FIG. 3. The data points that make up the plot in FIG. 4 can be measured at a sample rate having a predetermined frequency, such as 100 Hz or 200 Hz. Other frequencies could be implemented. In the example of FIG. 4, the pump is operating with a modulated speed range of about 2.375-3.125 krpm, with four modulations per 3-second window, equivalent to a heart rate of 80 beats per minute. The plot illustrated in FIG. 4 shows speed vs. position data points for a 3-second moving window, which form a hysteresis loop 110 representative of these parameters. The number of data points in the plot can vary depending on the configuration of the system. For instance, for a 3-second moving window and a sample rate of 200 Hz, the plot would include would be 600 data points, with the oldest being discarded from the 3-second window as new ones are added. It will therefore be appreciated that the number of data points in the plot can be increased or decreased through corresponding increases or decreases in the length of the window and/or the frequency of the sample rate. Example mean operating parameters for one point in this example plot are shown in the table below:

| PAP mmHg | AoP mmHg | RAP mmHg | LAP mmHg | KRPM | % Pos | Qright LPM |
|---|---|---|---|---|---|---|
| 21 | 81 | 0 | 5 | 2.75 | 49.2 | 5.0 |

ISP Equation 1 (reproduced in FIG. 4) calculates the area inside the hysteresis loop 110. For the 3-second window for the no suction condition of FIG. 4, the calculated ISP=6.0. Note that the shape of the hysteresis loop 110 is generally smooth/uniform, sits in the same position, and follows approximately the same path over the 3-second window. Under normal operating conditions, changes in the physiological condition of the patient due, for example, to changing activity levels, would manifest in slow, gradual changes in the shape or position of the hysteresis loop 110. These changes would be gradual in nature and should or would not rise to the level of triggering identification of a suction condition. Also, occurrences of hiccups, sneezing, falling, or sudden physical strain or exertion could change the shape of the loop. These occurrences require and are left for further study and design.

Viewing FIG. 3, when the pre-suction event takes place, flow is beginning to be obstructed at the right pump inlet 16, but only at peak speeds within the modulated speed cycle. While the pre-suction event does manifest itself in a cyclic reduction in right atrial pressure as expected, the change in rotor position is not as significant. The position signal remains symmetrical, the valleys narrow slightly, the peaks widen slightly, and the signal appears to shift slightly upward as viewed in FIG. 3. The pre-suction event can be characterized only as slightly significant because flow rate has not been affected.

When the right suction event takes place, the impact on the system is significant. The pulmonary arterial pressure becomes irregular and interrupted and the right atrial pressure drops precipitously. Left atrial pressure and right flow are affected slightly. The rotor position becomes unsymmetrical and skewed.

Figure 5:
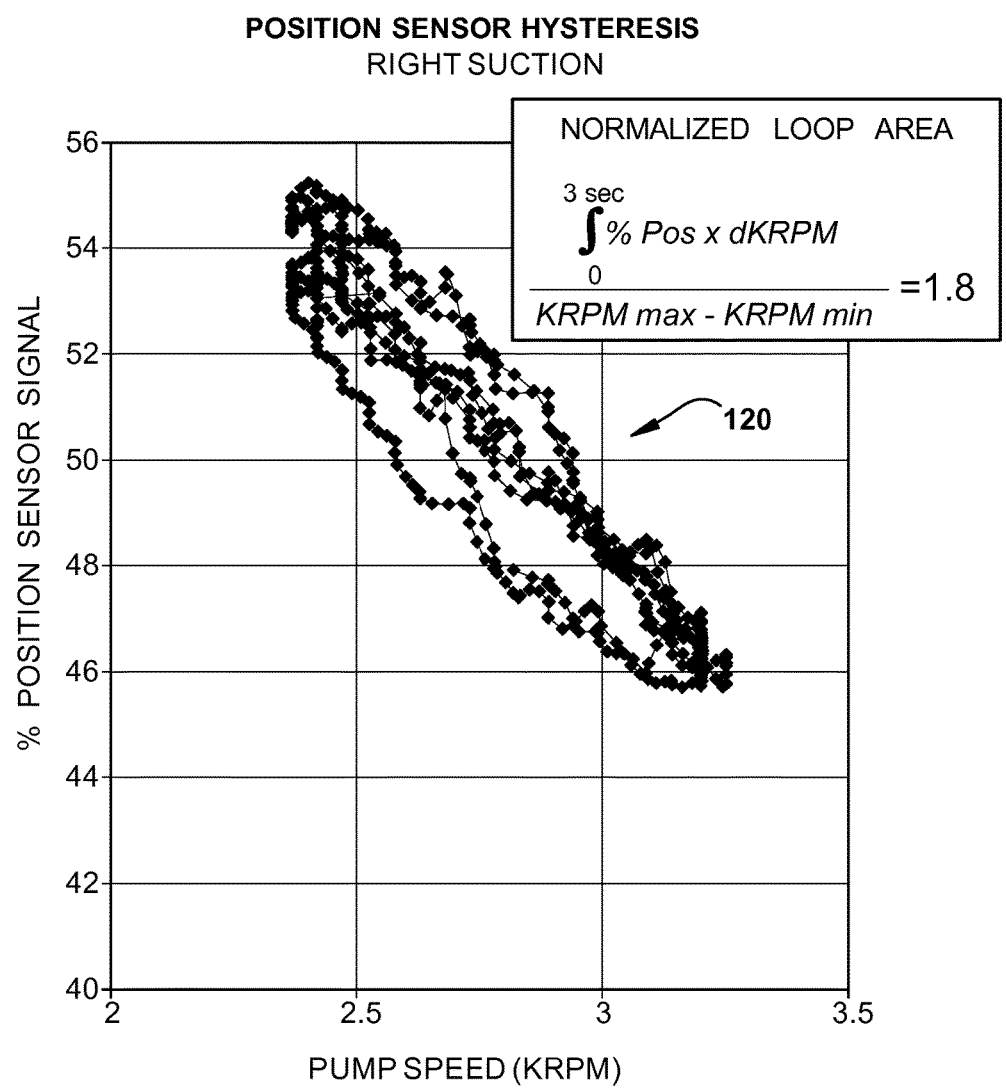

FIG. 5 is a plot that illustrates the pump rotor position versus speed during operation of the blood pump 10 in a right suction condition, such as the right suction condition illustrated in FIG. 3. The pump is operating with a modulated speed range of about 2.375-3.250 krpm, with four modulations per 3-second window. The plot illustrated in FIG. 5 shows speed vs. position data points for a 3-second moving window, which form a hysteresis loop 120 representative of these parameters. Example operating parameters for one point in this example plot are shown in the table below:

| PAP mmHg | AoP mmHg | RAP mmHg | LAP mmHg | KRPM | % Pos | Qright LPM |
|---|---|---|---|---|---|---|
| 19 | 82 | −6 | 3 | 2.80 | 50.1 | 4.5 |

ISP Equation 1 (reproduced in FIG. 5) calculates the area inside the hysteresis loop 120. For the 3-second window for the no suction condition of FIG. 4, the calculated ISP=1.8. Given that the ISP=6.0 for the non-suction event, this sudden 60% shift can be considered to be indicative of a suction condition. Note that the overall general shape and orientation of the hysteresis loop 120 in FIG. 5 is similar to the loop 110 in FIG. 4, but the plotted points and the lines generated therefrom are irregular and deviate from one another to the point that some of the points are positioned within the loop 120 instead of helping to form the outline of the loop, thus contributing to the smaller loop area of the calculated ISP.

When both the right and left suction event takes place, the impact on the system is severe. The pulmonary arterial pressure becomes completely interrupted and irregular and the right atrial pressure drops precipitously and becomes interrupted. Left atrial pressure drops and right flow is interrupted. The rotor position signal becomes interrupted and irregular.

Figure 6:
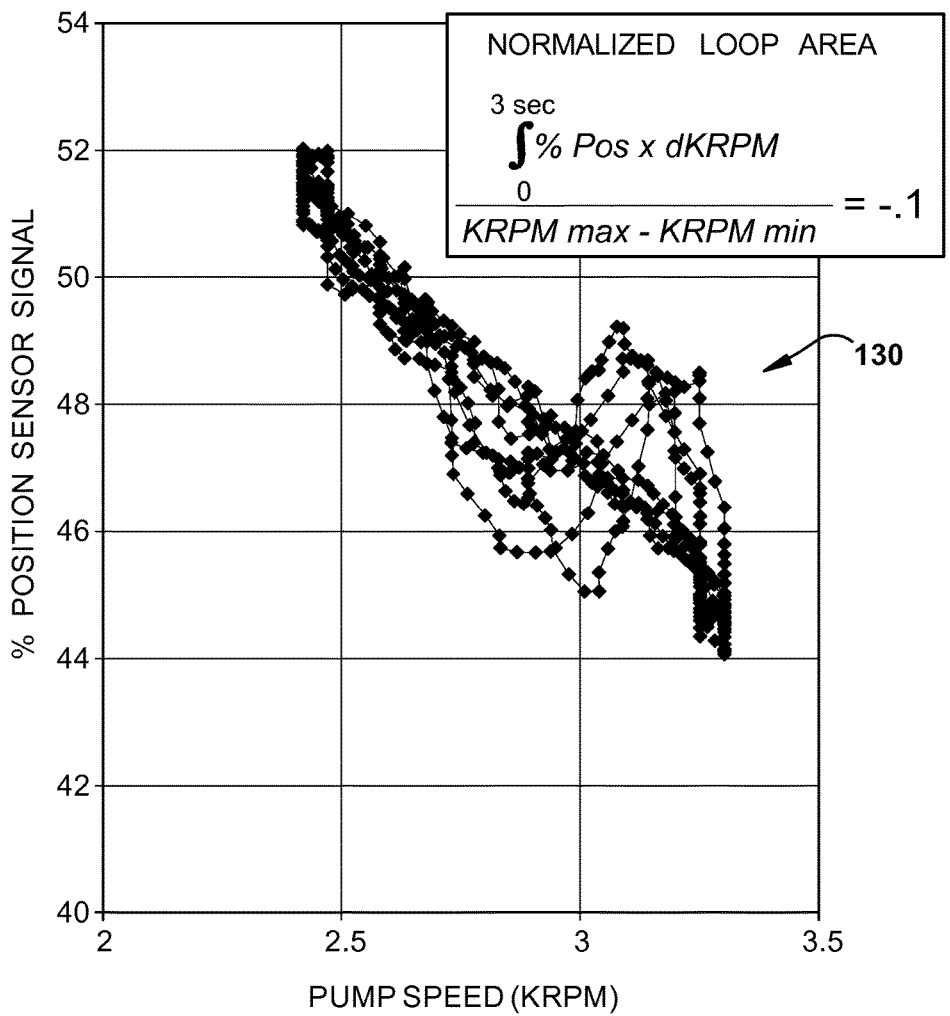

FIG. 6 is a plot that illustrates the pump rotor position versus speed during operation of the blood pump 10 in a right and left suction condition, such as the right and left suction condition illustrated in FIG. 3. The pump is operating with a modulated speed range of about 2.375-3.250 krpm, with four modulations per 3-second window. The plot illustrated in FIG. 6 shows speed vs. position data points for a 3-second moving window, which form a hysteresis loop 130 representative of these parameters. Example operating parameters for one point in this example plot are shown in the table below:

| PAP mmHg | AoP mmHg | RAP mmHg | LAP mmHg | KRPM | % Pos | Qright LPM |
|---|---|---|---|---|---|---|
| 16 | 76 | −9 | −7 | 2.85 | 48.2 | 4.95 |

ISP Equation 1 (reproduced in FIG. 6) calculates the area inside the hysteresis loop 130. For the 3-second window for the no suction condition of FIG. 4, the calculated ISP=−0.1. Given that the ISP=6.0 for the non-suction event, this sudden 100% shift indicative of a suction condition. Note that the hysteresis loop 130 in FIG. 6 does not have even the general form of a loop and that the plotted points and the lines generated therefrom are highly irregular and deviate greatly from one another to the point that in no part of the plot is there an area that resembles or can be considered a loop compared, for example, to the loop 110 of FIG. 4.

From the above, it will be appreciated that the artificial heart system 100 can be configured and implemented to identify an inlet suction condition based on a system condition parameter that is calculated on the basis of a relationship with a system operating parameter which, according to this aspect of the invention, is rotor axial position hysteresis. According to this determination, a rotor position hysteresis loop is calculated at a predetermined frequency and for a predetermined time period (i.e., window). For each loop collected in that window, an impending suction parameter (ISP) related to the area within the loop is calculated. As the window proceeds or moves over time, the area within the loop is re-calculated at the predetermined frequency and compared to an average or composite of the previous loops within the window. If a deviation indicative of the occurrence of a suction condition has occurred, the controller 32 responds accordingly, e.g., by decreasing pump speed and issuance of a warning or alarm.

Power Hysteresis Suction Identification

Another system operating parameter for which hysteresis can be used to calculate a system condition parameter is motor power. In the artificial heart system 100 described herein, power is a function of speed and flow and, without obstruction, the power and flow will rise and fall with speed. The controller 32 tracks speed and power with every speed modulation cycle, and is plotted as a narrow hysteresis loop of normalized power (Watts/krpm$^2$) vs. speed (krpm). Since normalized power is directly related to flow, this hysteresis loop is analogous to flow vs. speed. In this way, the flow vs. speed characteristic is tested with every simulated heartbeat, and any change in this characteristic reflects an actual change in the inlet or outlet environment of the pump. At the start of suction, the area of the normalized power vs. speed hysteresis loop changes in shape and increases in area as fluid availability diminishes as a result of the peak modulating flows. This property of normalized power vs. speed loop area is used as the basis for this sensorless suction recognition parameter.

According to this aspect of the invention, the controller 32 can implement an algorithm that identifies a suction condition based on normalized motor power hysteresis. To achieve this, referring to FIG. 1, the artificial heart system 100 is adapted so that the controller 32 implements a control algorithm that monitors pump power in real time during operation of the blood pump 10. According to this aspect of the invention, suction at one or more of the pump inlets 14, 16 can be identified by modulating pump speed and monitoring a hysteresis loop of the resulting power consumed by the pump 10.

According to this aspect of the invention, the controller 32 can implement an algorithm that identifies a suction condition based on the evaluation of a pump power hysteresis loop. According to this algorithm, pump speed is modulated to produce pulsatile flow. Due to this modulation, the pump's normalized power vs. speed characteristic manifests as a hysteresis loop. Suction at one or more of the pump inlets is identified by monitoring changes in the hysteresis loop. To monitor the hysteresis loop, the area of the loop is continuously evaluated through numerical integration to identify changes in the shape of the loop. This property of loop area (normalized power vs. speed) is used as the basis for a suction avoidance parameter of the control algorithm implemented in the controller 32.

Under normal pump operating conditions, the hysteresis loop will take on a general shape that does not does not deviate significantly unless the conditions of the physiology of the patient or the operating parameters of the artificial heart system 100 change. Even so, slight or gradual changes in these conditions/parameters are expected, so the shape of the hysteresis loop would be expected to change correspondingly slightly or gradually over time. Deviations in the shape of the hysteresis loop that fall outside these expected changes to a significant degree can be indicative of a suction event. According to this aspect of the invention, the artificial heart system 100 is constructed and configured to monitor the shape of the hysteresis loop for deviations from the expected shape. To accomplish this, an integral equation is implemented by the controller 32, which calculates the area within the loop at a predetermined frequency. This area is summed within a moving time window, such as a 3-second moving window, although shorter or longer windows can be implemented. Deviations in the calculated hysteresis loop from the values expected based on the moving window can be characterized as indicating a suction condition.

For example, according to one implementation, the controller 32 can acquire data points at a predetermined frequency, such as 100 Hz or 200 Hz, to form or otherwise identify the hysteresis loop. The controller 32 can calculate the area within the loop over a 3-second window. Within this window, the controller 32 can calculate the area at a predetermined frequency, such as once per second or once per speed modulation. Thus, for example, with a 3-second window, the controller 32 could perform an integral calculation, every second, of the area within the loop for the last three seconds. As the window moves along in time, new loop calculations are added and the oldest is removed on a first-in, first-out basis, thus creating a moving 3-second window. Each new loop area calculation can be compared to one or more of the previously calculated loop areas or to a composite or average of the previous loop areas. If the area of the new loop deviates by a predetermined amount or limit value from those in the previous loops, this can indicate a suction event and the controller 32 can respond appropriately, e.g., by producing an alarm and reducing pump speed.

According to this aspect of the invention, the normalized power vs. speed characteristics of the system 100 are monitored via a hysteresis loop. To accomplish this, the controller 32 can implement a computer program to calculate an Impending Suction Parameter (ISP) to evaluate hysteresis in the system operating parameter which, according to this aspect of the invention, is motor power. The ISP can be tested against a limit value to trigger a speed control response. The normalized motor power (Watts/krpm$^2$) is integrated with respect to speed over an integer number of speed cycles within the previous 3-sec data cycle. This integration can, for example, be performed once per second.

The resulting area will be normalized by dividing by speed range, resulting in an Impending Suction Parameter (ISP) as follows:

$$ISP = \frac{\int_{t=0}^{t=n\,sec} \frac{P(t)}{N(t)^2} dN}{N_{max} - N_{min}} \text{ (Watts/krpm}^2\text{)} \quad \text{(Equation 2)}$$

where P(t)=motor power (Watts), N(t)=pump speed (krpm), $N_{max}$-$N_{min}$ is the modulated speed range, and n sec is the time interval of the integral in seconds (e.g., 3 seconds).

The integration can be performed within the controller 32 in any known manner. For example, the controller 32 can perform a simple numerical integration method, such as the Trapezoidal Rule or Simpson's Rule. The speed modulation rate can, for example, be set conveniently to 60, 80, 100, or 120 BPM, such that there will be an integer number (n=3, 4, 5 or 6) of speed modulation cycles over the 3-second integration period. Other known integration methods, such as Boole's Rule, Hardy's Rule, Newton-Cotes Formulas, Simpson's ⅜ Rule, or Weddle's Rule could also be utilized. The integration period could also be increased or decreased, and alternative speed modulation rates could be selected.

Figure 7B:
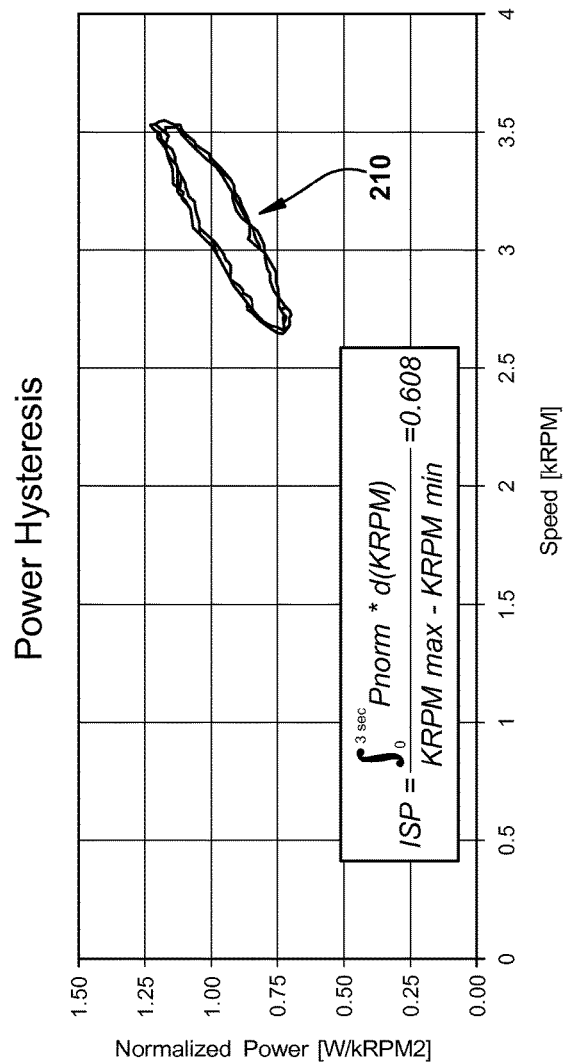
Figure 7A:
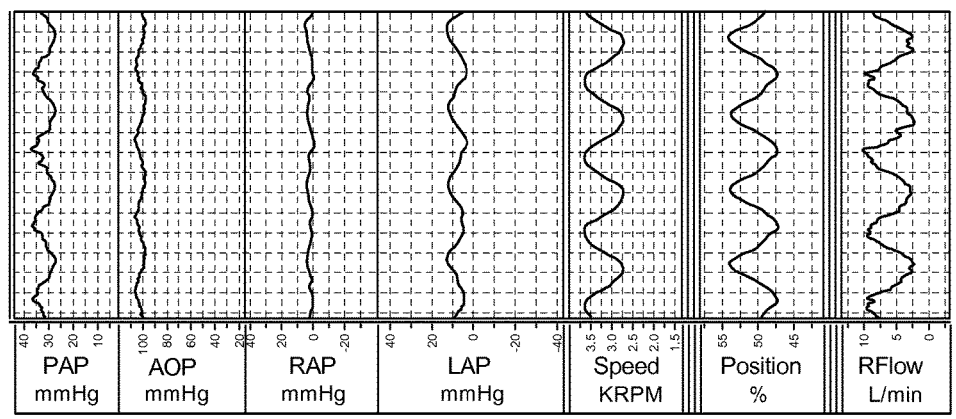
Figure 9B:
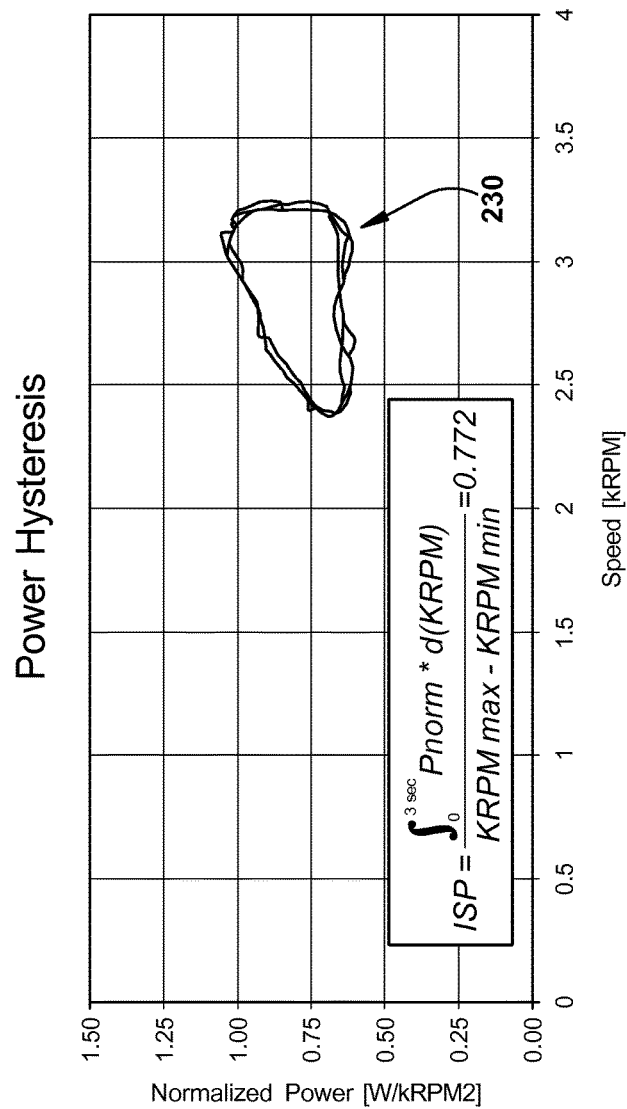
Figure 9A:
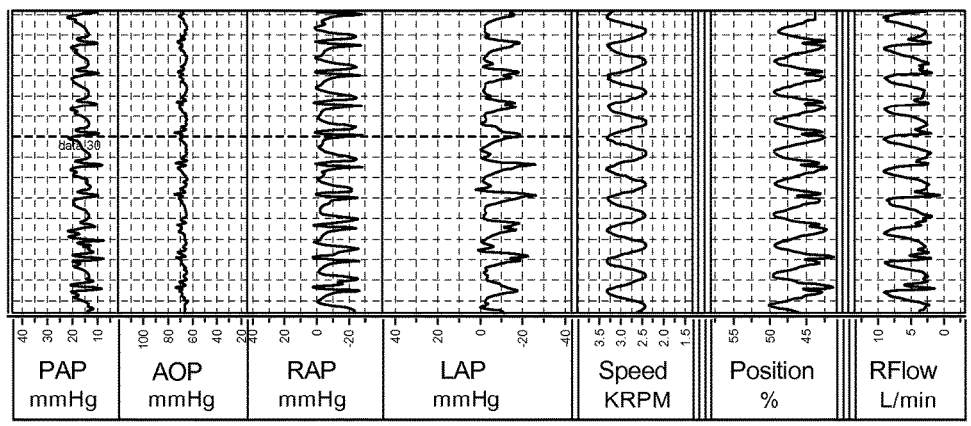

FIGS. 7A, 8A, and 9A illustrates certain physiological and pump characteristics and system operating parameters during operation of the blood pump 10 in-vivo in the in-vivo-subject. The characteristics/parameters illustrated in these Figures include pulmonary arterial pressure or "PAP" (mmHg), aortic (left outlet) pressure or "AoP" (mmHg), right atrial pressure or "RAP" (mmHg), left atrial pressure or "LAP" (mmHg), motor speed (krpm), rotor position, and right flow or "Rflow" (liter/min, LPM). FIGS. 7A, 8A, and 9A illustrate these characteristics over a 3-second window.

FIG. 7A illustrates a no-suction condition. Viewing the no suction condition, it is readily apparent that as the pump speed is modulated, there is a corresponding modulation in the physiological and pump characteristics and system operating parameters. The modulation in these conditions varies in amplitude, but the period of these conditions is approximately equal to the modulated speed. Of particular note is that the phase of these conditions is shifted from the modulated speed. This illustrates the dependent, time-shifted nature of these interrelated conditions which gives rise to hysteresis in the system.

FIG. 7B is a plot that illustrates the pump normalized power versus speed during operation of the blood pump 10 in the no suction condition illustrated in FIG. 7A. The pump is operating with a modulated speed range of about 2.7-3.6 krpm, with four speed modulations over the 3-second window. The plot illustrated in FIG. 7B shows speed vs. normalized power data points within the 3-second moving window of FIG. 7A, which form a hysteresis loop 210 representative of these parameters.

ISP Equation 2 (reproduced in FIG. 7B) calculates the area inside the hysteresis loop 210. For the 3-second window for the no suction condition of FIG. 7B, the calculated ISP=0.608. Note that the shape of the hysteresis loop 210 is generally smooth/uniform over the recorded iterations. Each of the iterations sits in the same general position, and follows approximately the same path over the 3-second window. Under normal operating conditions, changes in the physiological condition of the patient due, for example, to changing activity levels, would manifest in slow, gradual changes in the shape or position of the hysteresis loop 210. These changes would be gradual in nature and should or would not rise to the level of triggering identification of a suction condition.

FIG. 8A illustrates a suction condition. Viewing the suction condition, it is readily apparent that as the pump speed is modulated, there is a corresponding modulation in the physiological and pump characteristics. The suction condition has the effect of introducing irregularities into the illustrated characteristics. Of particular note are the effects that the suction condition has on the PAP, AoP, RAP, and Rflow.

FIG. 8B is a plot that illustrates the pump normalized power versus speed during operation of the blood pump 10 in the no suction condition illustrated in FIG. 8A. The pump is operating with a modulated speed range of about 2.7-3.6 krpm, with four modulations over the 3-second window. The plot illustrated in FIG. 8B shows speed vs. normalized power data points for the 3-second moving window of FIG. 8A, which form a hysteresis loop 220 representative of these parameters.

ISP Equation 2 (reproduced in FIG. 8B) calculates the area inside the hysteresis loop 220. For the 3-second window for the no suction condition of FIG. 8B, the calculated ISP=1.006. Given that the ISP=0.608 for the non-suction event, this sudden increase is indicative of a suction condition. Note that the hysteresis loop 220 no longer follows the generally smooth/uniform pattern over the four recorded iterations. Instead, the lower portions of the loops are distorted and non-uniform which leads to the increase in the calculated ISP.

FIG. 9A illustrates a severe suction condition. Viewing the suction condition, it is readily apparent that as the pump speed is modulated, there is a corresponding modulation in the physiological and pump characteristics. The suction condition has the effect of introducing severe irregularities into the illustrated characteristics. Of particular note are the effects that the suction condition has on the PAP, AoP, RAP, and Rflow.

FIG. 9B is a plot that illustrates the pump normalized power versus speed during operation of the blood pump 10 in the no suction condition illustrated in FIG. 9A. The pump is operating with a modulated speed range of about 2.350-3.250 krpm, with four modulations over the 3-second window. The plot illustrated in FIG. 8B shows speed vs. normalized power data points for the 3-second moving window of FIG. 9A, which form a hysteresis loop 230 representative of these parameters.

ISP Equation 2 (reproduced in FIG. 9B) calculates the area inside the hysteresis loop 230. For the 3-second window for the no suction condition of FIG. 9B, the calculated ISP=0.772. Note that the hysteresis loop 230 no longer follows the generally smooth/uniform pattern over the four recorded iterations. Instead, the lower portions of the loops are distorted and non-uniform which leads to the increase in the calculated ISP. Note also that the lower operating speed of the pump results in lower power consumption, as expected, but note also that this only has the effect of shifting the loop 230 downward and to the left, as viewed in FIG. 9B.

From the above, it will be appreciated that the artificial heart system 100 can be configured and implemented to identify an inlet suction condition based on a system condition parameter calculated according to a relationship with a system operating parameter. According to this aspect of the invention, this system operating parameter can be motor power hysteresis. According to this determination, a normalized power hysteresis loop is calculated for a predetermined time period (i.e., window). For the loop collected in that window, the area within the loop is calculated. As the window proceeds or moves over time, the area within the loop is re-calculated at predetermined intervals and compared to previous windows/loops to evaluate whether a deviation indicative of the occurrence of a suction condition has occurred.

Current Error Suction Identification

It was observed by examination of in vivo experimental data, that the CFTAH current response to a given speed modulation, changes with hemodynamic conditions. This offers an opportunity to use the current response for monitoring and reporting changes in the patient's condition, and to identify when a speed reduction is needed to avoid suction.

Figure 10A:
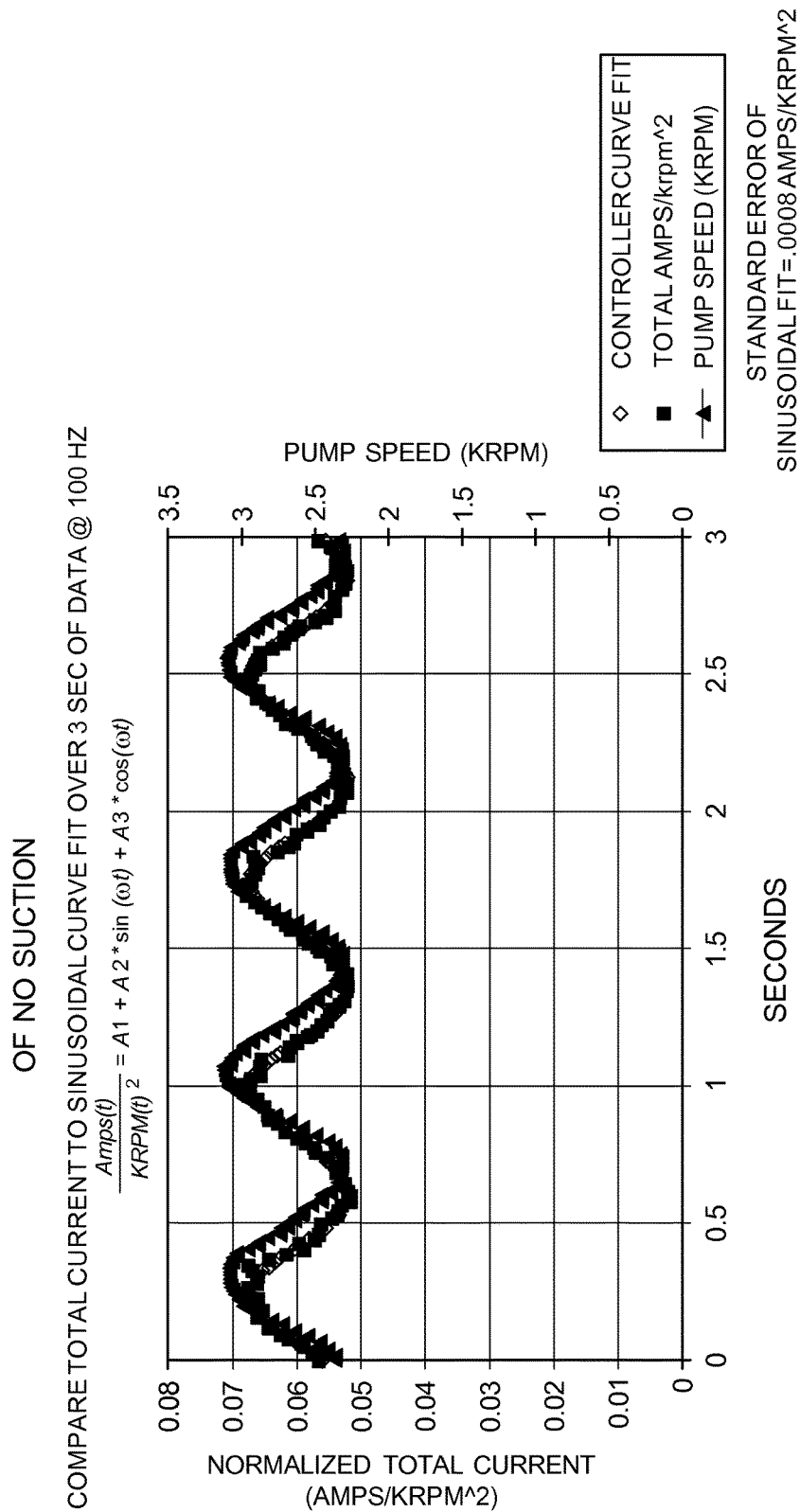
FIGS. 10A-10B are charts that illustrate the identification of pump inlet suction, according to another aspect of the invention.

To investigate this, a statistical analysis method was created using a sine function series to determine a normalized current function (NCF):

$$NCF = A1 + A2^*\sin(\omega t) + A3^*\cos(\omega t); \quad \text{(Equation 3)}$$

where $\omega$=speed modulation frequency (rad/sec), and t=seconds, with constants A1 thru A3 to be determined by real time linear regression to match the actual normalized current wave form (amps/krpm$^2$). An example plot showing the actual normalized current and NCF is shown in FIG. 10A. The normalized current was determined using different hemodynamic conditions from in-vivo data of speed and current, recorded via a data acquisition system (e.g., Power Lab), at a predetermined frequency and for a predetermined duration (e.g., 200 Hz, for 3 seconds). Alternative sampling rates and durations, such as 100 Hz for 2 seconds, could also be used. An integer number of cycles is not required for this approach.

Through the above process, it was determined that the resulting periodic function of the normalized current during normal operation was similar to the sinusoidal speed input.

Figure 10B:
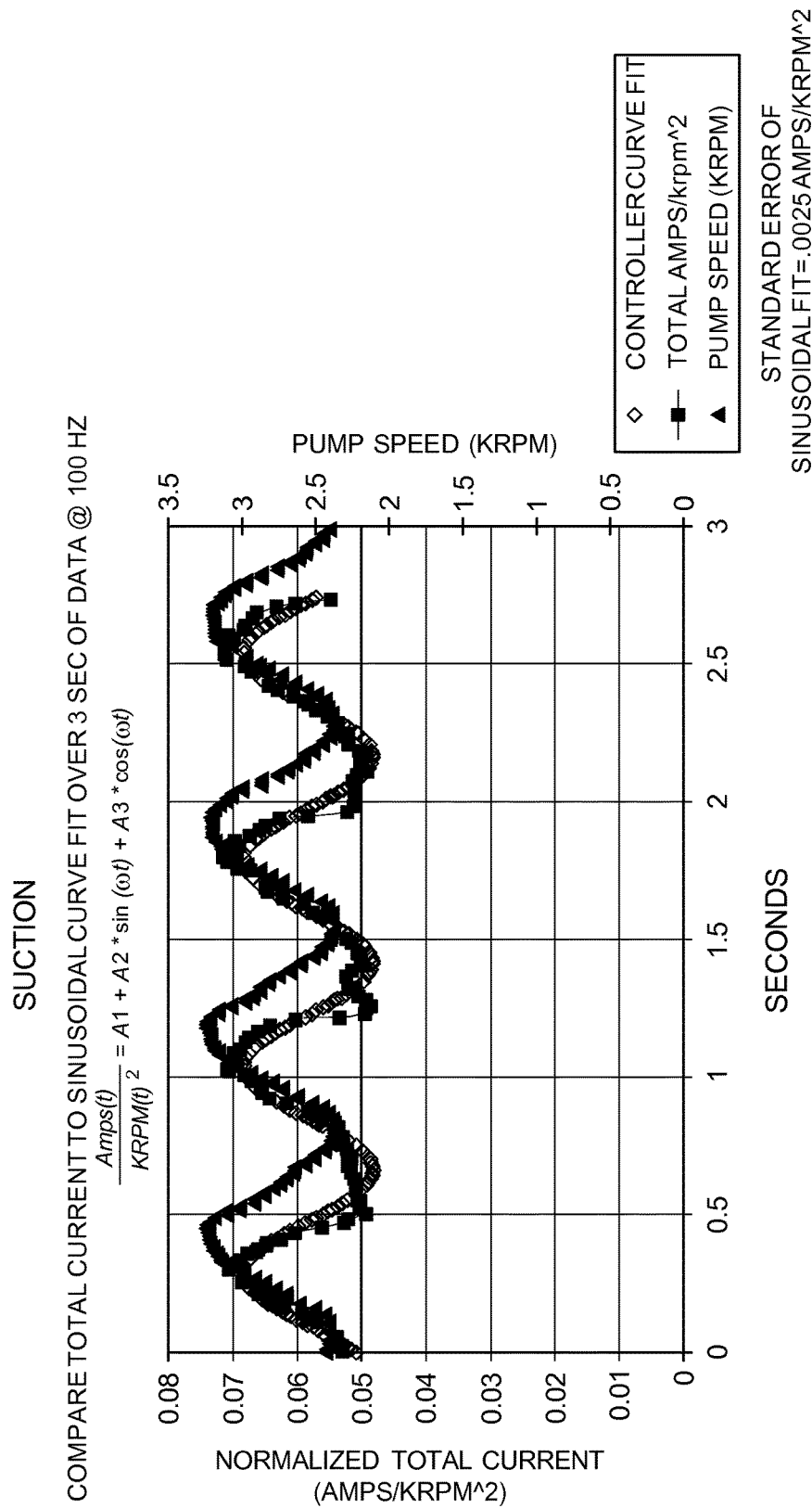

With higher pump speeds, the system can be driven into inlet suction, which produces a normalized current relationship that is too complex for the two term sine function curve fit of the NCF to follow. This is shown in FIG. 10B. The resulting suction condition can be identified by standard error of the fit to the actual normalized current. Therefore, according to this aspect of the invention, the standard error in the NCF function can be used to identify the suction condition. For instance, the controller 32 could be programmed to identify a suction condition when the standard error reaches or exceeds 0.015 and to trigger a warning, alarm, or speed decrement as an introductory method of responding to and avoiding suction.

Suction Recognition and Avoidance Methods

From the above, it will be appreciated that the artificial heart system 100 can implement a method for controlling operation of the system. Some methods that the system 100 can implement are illustrated in FIGS. 11A-11E. In the block diagrams shown in these figures, certain steps of the methods are illustrated sequentially. The sequence of these steps is illustrative only of an example methodology implemented by the system 100 and is not necessarily meant to be limiting. It should be appreciated that certain ones of these steps can be repeated, can be performed out of sequence, and can be performed simultaneously.

Figure 11A:
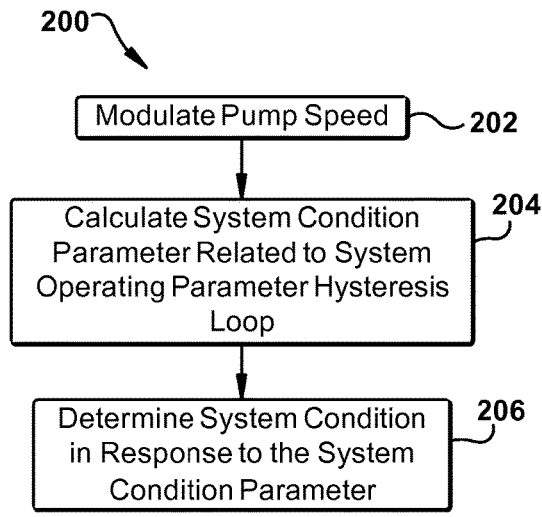
FIGS. 11A-11E are block diagrams that illustrate methods implemented by the total artificial heart system, according to another aspect of the invention.

Referring to FIG. 11A, according to one aspect, the method 200 includes the step 202 of modulating the speed of the pump, and the step 204 of calculating a system condition parameter having a value related to a hysteresis loop generated by a system operating parameter that varies in response to pump speed. The method 200 includes the further step 206 of determining the condition of the system in response to the value of the system condition parameter.

Figure 11B:
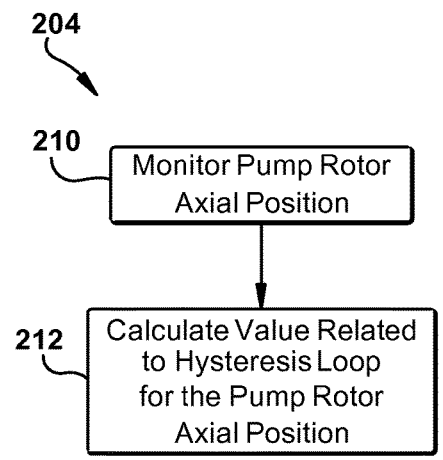

Referring to FIG. 11B, according to another aspect, the step 204 of calculating the system condition parameter comprises the step 210 of monitoring the pump rotor axial position and the step 212 of calculating a value related to a hysteresis loop for the pump rotor axial position.

Figure 11C:
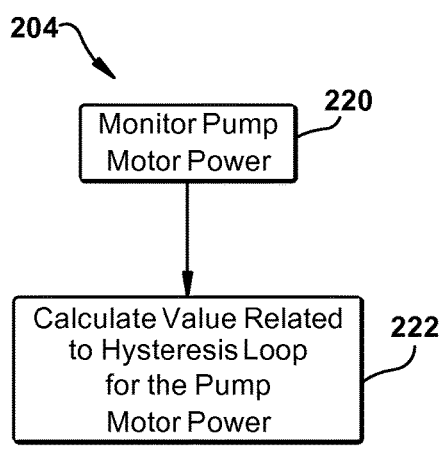

Referring to FIG. 11C, according to another aspect, the step 204 of calculating the system condition parameter comprises the step 220 of monitoring the pump motor power and the step 222 of calculating a value related to a hysteresis loop for the pump motor power.

Figure 11D:
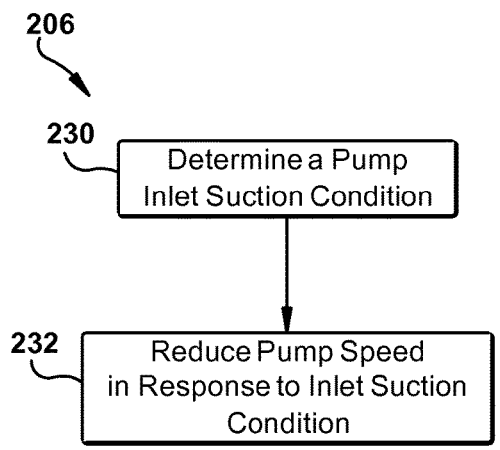

Referring to FIG. 11D, according to another aspect, the step 206 of determining the condition of the system comprises the step 230 of determining a pump inlet suction condition, and the step 232 of reducing the speed of the pump in response to determining a pump inlet suction condition.

Figure 11E:
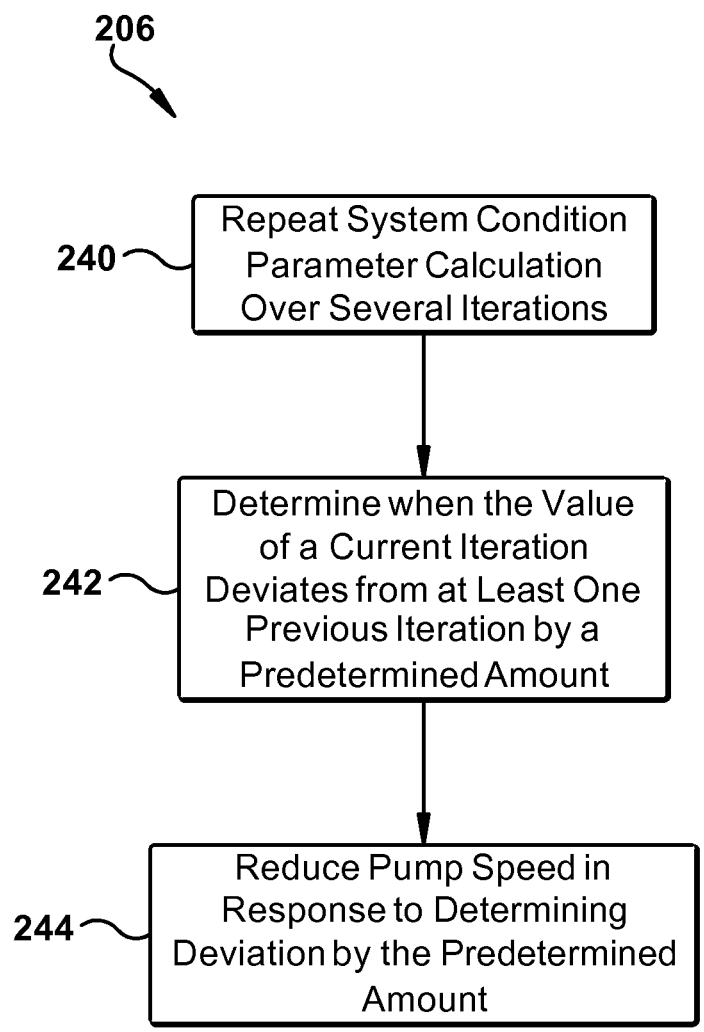

Referring to FIG. 11E, according to another aspect, the step 206 of determining the condition of the system comprises the step 240 of repeating the calculation of the system condition parameter over several iterations. The step 206 also includes the step 242 of determining when the value of a current iteration of the calculated system condition parameter deviates from a limit value by a predetermined amount. The step 206 further includes the step 244 of reducing the speed of the pump in response to determining the amount of deviation.

The foregoing has described an artificial heart system implementing suction recognition and avoidance methods. While specific embodiments of the invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

What is claimed is:

1. A method of controlling the operation of a pump system, the method comprising:
   modulating the speed of a pump;
   monitoring a system operating parameter that varies in response to modulating the speed of the pump;
   calculating hysteresis in the system operating parameter resulting from modulating the speed of the pump;
   determining an expected value for the hysteresis;
   determining a pump inlet suction condition of the pump system in response to the calculated hysteresis deviating from the expected value; and
   reducing the speed of the pump in response to determining the pump inlet suction condition.

2. The method recited in claim 1, wherein the system operating parameter comprises pump rotor axial position.

3. The method recited in claim 1, wherein the system operating parameter comprises motor power of the pump.

4. The method recited in claim 1, wherein the pump comprises a blood pump.

5. The method recited in claim 1, wherein:
   calculating hysteresis comprises performing an integral calculation on the system operating parameter; and
   determining the expected value for the hysteresis comprises summing a total of the integral calculation over a moving time window.

6. The method recited in claim 5, wherein modulating the pump speed comprises performing an integer number of modulations within the time window.

7. A method of controlling the operation of a pump system, the method comprising:
modulating the speed of a pump;
calculating a system condition parameter having a value related to a hysteresis loop generated by a system operating parameter that varies in response to pump speed;
determining a pump inlet suction condition of the pump system in response to the value of the system condition parameter, wherein the system operating parameter comprises pump rotor axial position, and wherein the system condition parameter is calculated according to:

$$ISP = \frac{\int_{t=0}^{t=n\,sec} L(t)dN}{N_{max} - N_{min}}$$

wherein L(t) is the pump rotor axial position, $N_{max}$-$N_{min}$ is a modulated speed range, dN is the change in pump speed, and n sec is the time interval of the integral in seconds; and
reducing the speed of the pump in response to determining the pump inlet suction condition.

8. A method of controlling the operation of a pump system, the method comprising:
modulating the speed of a pump;
calculating a system condition parameter having a value related to a hysteresis loop generated by a system operating parameter that varies in response to pump speed;
determining a pump inlet suction condition of the pump system in response to the value of the system condition parameter, wherein the system operating parameter comprises motor power of the pump, and wherein the system condition parameter is calculated according to:

$$ISP = \frac{\int_{t=0}^{t=n\,sec} \frac{P(t)}{N(t)^2}dN}{N_{max} - N_{min}}$$

wherein P(t) is the pump motor power, N(t) is the pump speed, $N_{max}$-$N_{min}$ is a modulated speed range, dN is the change in pump speed, and n sec is the time interval of the integral in seconds; and
reducing the speed of the pump in response to determining the pump inlet suction condition.

9. A pump system comprising: a pump; and a pump controller configured to: modulate the speed of the pump; monitor a system operating parameter that varies in response to modulating the speed of the pump; calculate hysteresis in the system operating parameter resulting from modulating the speed of the pump; determine an expected value for the hysteresis; determine an undesired a pump inlet suction condition of the pump system in response to the calculated hysteresis deviating from the expected value; and reduce the speed of the pump in response to determining the pump inlet suction condition.

10. The system recited in claim 9, wherein the system operating parameter comprises pump rotor axial position.

11. The system recited in claim 9, wherein the system operating parameter comprises motor power of the pump.

12. The system recited in claim 9, wherein to determine the condition of the system, the pump controller is adapted to:
repeat the calculation of the system condition parameter over several iterations; and
determine when the value of a current iteration of the calculated system condition parameter deviates from a limit value by a predetermined amount.

13. The system recited in claim 9, wherein the pump comprises a blood pump.

14. The system recited in claim 9, wherein the pump comprises an electrical motor coupled to a rotor that carries first and second impellers at opposite ends thereof.

15. The system recited in claim 14, wherein the pump comprises an artificial heart, wherein the first impeller communicates with a patient's systemic vasculature and the second impeller communicates with the patient's pulmonary vasculature, the pump being operable to circulate blood from the first impeller through the systemic vasculature to the second impeller, and from the second impeller through the pulmonary vasculature back to the first impeller.

16. The system recited in claim 9, wherein the controller is further configured to:
calculate the hysteresis by performing an integral calculation on the system operating parameter; and
determine the expected value for the hysteresis by summing a total of the integral calculation over a moving time window.

17. The system recited in claim 16, wherein the controller is further configured to modulate the pump speed by performing an integer number of modulations within the time window.

18. A pump system comprising:
a pump; and
a pump controller adapted to calculate a system condition parameter having a value related to a hysteresis loop generated by a system operating parameter that varies in response to pump speed, and determine the condition of the pump system in response to the value of the system condition parameter, wherein the system operating parameter comprises pump rotor axial position, and wherein the system condition parameter is calculated according to:

$$ISP = \frac{\int_{t=0}^{t=n\,sec} L(t)dN}{N_{max} - N_{min}}$$

wherein L(t) is the pump rotor axial position, $N_{max}$-$N_{min}$ is a modulated speed range, dN is the change in pump speed, and n sec is the time interval of the integral in seconds; and
wherein the pump controller is adapted to determine a pump inlet suction condition in response to the system condition parameter and to reduce the speed of the pump in response to determining the pump inlet suction condition.

19. A pump system comprising:
a pump; and
a pump controller adapted to calculate a system condition parameter having a value related to a hysteresis loop generated by a system operating parameter that varies in response to pump speed, and determine the condition of the pump system in response to the value of the system condition parameter, wherein the system operating parameter comprises motor power of the pump, and wherein the system condition parameter is calculated according to:

$$ISP = \frac{\int_{t=0}^{t=n\,sec} \frac{P(t)}{N(t)^2} dN}{N_{max} - N_{min}}$$

wherein P(t) is the pump motor power, N(t) is the pump speed, $N_{max}$-$N_{min}$ is a modulated speed range, dN is the change in pump speed, and n sec is the time interval of the integral in seconds; and wherein the pump controller is adapted to determine a pump inlet suction condition in response to the system condition parameter and to reduce the speed of the pump in response to determining the pump inlet suction condition.

* * * * *

UNITED STATES PATENT AND TRADEMARK OFFICE
CERTIFICATE OF CORRECTION

PATENT NO.        : 10,077,777 B2
APPLICATION NO.   : 14/273854
DATED             : September 18, 2018
INVENTOR(S)       : David J. Horvath et al.

Page 1 of 1

It is certified that error appears in the above-identified patent and that said Letters Patent is hereby corrected as shown below:

Column 17, Line 56 reads "an undesired a pump" should read --a pump--

Signed and Sealed this
Thirteenth Day of November, 2018

Andrei Iancu
*Director of the United States Patent and Trademark Office*